United States Patent [19]

Houtman

[11] Patent Number: 5,446,777
[45] Date of Patent: Aug. 29, 1995

[54] POSITION-SENSITIVE X-RAY ANALYSIS

[75] Inventor: Eliberthus Houtman, Almelo, Netherlands

[73] Assignee: U.S. Philips Corporation, New York, N.Y.

[21] Appl. No.: 287,053

[22] Filed: Aug. 8, 1994

Related U.S. Application Data

[63] Continuation of Ser. No. 8,113, Jan. 25, 1993, abandoned.

[30] Foreign Application Priority Data

Jan. 27, 1992 [EP] European Pat. Off. ............ 92200208

[51] Int. Cl.$^6$ ............................................. G01N 23/02
[52] U.S. Cl. ........................................ 378/45; 378/55; 378/79
[58] Field of Search .................. 378/69, 71, 51, 73, 378/76, 53, 45, 49, 116, 79, 205, 56, 55, 147, 151

[56] References Cited

U.S. PATENT DOCUMENTS

| | | |
|---|---|---|
| 2,853,618 | 9/1958 | De Marco et al. |
| 3,428,802 | 2/1969 | Mehta et al. ............... 378/71 |
| 4,076,981 | 2/1978 | Sparks et al. ............. 378/71 |
| 4,910,758 | 3/1990 | Herrick ................... 378/71 |
| 5,268,953 | 12/1993 | Van Vlijmen ............. 378/79 |

FOREIGN PATENT DOCUMENTS

| | | |
|---|---|---|
| 3839990 | 6/1989 | Germany . |
| 59-007251 | 4/1984 | Japan . |
| 61-256243 | 4/1987 | Japan . |
| 4-236348 | 12/1992 | Japan . |

*Primary Examiner*—David P. Porta
*Assistant Examiner*—Don Wong
*Attorney, Agent, or Firm*—Michael J. Balconi-Lamica; Anne E. Barschall

[57] ABSTRACT

For position-sensitive measurements, an X-ray analysis system comprises a one-dimensional position-sensitive detector and a detection Soller slit system in order to achieve position sensitivity in a direction transversely of the dispersion direction of the detector. Different position-sensitive measurement methods can be carried out by adaptation of the Soller slit system and the orientation of the one-dimensional position-sensitive detector.

10 Claims, 2 Drawing Sheets

POSITION-SENSITIVE X-RAY ANALYSIS

This is a continuation of application Ser. No. 08/008,113, filed on Jan. 25, 1993 now abandoned.

The invention relates to an X-ray analysis apparatus, comprising an X-ray source for generating an X-ray beam for irradiating an object to be analysed, an object holder for object positioning, a detection system for detection of X-rays emanating from the object, and an angulation mechanism.

An X-ray analysis apparatus of this kind is known from U.S. Pat. No. 2,853,618. An apparatus described therein simultaneously measures an object surface equal to the local beam cross-section in an integrated manner. Measurements on a larger object surface necessitate a translation between the irradiating beam and the object.

There is a growing demand for position-sensitive analysis of an object with a comparatively high spatial resolution, i.e. analysis per comparatively small surface area.

A solution in this respect is described in DE 38 39 990. An apparatus described therein enables position-sensitive measurement by utilizing a composite slit collimator system and a two-dimensional position-sensitive detector. The object surface to be analysed is then subdivided into a number of sub-regions to be simultaneously irradiated but separately analysed. The slit collimator system provides the subdivision in a first direction and the position-sensitive detector provides the subdivision in a second direction, so that a two-dimensional subdivision of the simultaneously irradiated surface is obtained. A second dimension of the two-dimensional position-sensitive detector provides the desired $2\theta$ angulation in the apparatus.

A detection system comprising a two-dimensional position-sensitive detector is comparatively expensive and its resolution is insufficient for many analysis applications. The slit collimator system of the known apparatus is comparatively complex and restricts the freedom of use of a plurality of analysis methods.

It is an object of the invention to provide an apparatus in which said drawbacks are reduced; to achieve this, an X-ray analysis apparatus of the kind set forth is characterized in that the angulation mechanism, a one-dimensional position-sensitive detector and a detection collimator system are constructed and arranged relative to one another so as to achieve simultaneous, position-dependent analysis of an instantaneously irradiated part of the object, see e.g. FIG. 4.

Because an apparatus in accordance with the invention utilizes a one-dimensional position-sensitive detector, it can be substantially cheaper, a higher resolution can be achieved and the construction of the detector read-out system can also be substantially simpler. Moreover, a substantially simpler collimator system can be used.

In a preferred embodiment, a position-sensitive direction of the one-dimensional position-sensitive detector coincides with a $2\theta$ angulation mechanism. Using an arrangement of this kind, the position-sensitive detector can be used for angle-dependent read-out in the $2\theta$ angulation direction and can replace as such the customary $2\theta$ angulation mechanism.

A further preferred embodiment in accordance with the invention comprises an elongate detection slit having a longitudinal direction with which the position-sensitive direction of the one-dimensional position-sensitive detector is coincident. In the absence of the collimator, see FIG. 3 variation in diffraction lines in the longitudinal direction of the detection slit, for example due to the coarse grains of a specimen to be analysed, can thus be measured in a simple manner. The longitudinal direction of the detection slit is then oriented perpendicularly to the diffraction plane. The diffraction plane is a plane extending transversely of the line focus and centrally through the analysis beam.

A further preferred embodiment comprises a detection slit with a one-dimensional position-sensitive detector which is situated in the longitudinal direction thereof and with a slit collimator system for position-sensitive analysis of an object to be analysed. Using such a construction, two-dimensional position-sensitive measurement can be performed in a comparatively simple manner. Moreover, stress measurements, phase analysis as well as texture measurements can thus be performed on bulk material.

In the case of position-sensitive measurements, only a small surface of the object to be analysed will be considered per measuring channel. Consequently, the counting statistics in the measuring channel will be comparatively low. In order to improve this, a preferred embodiment provides oscillation of the object relative to the X-ray source and the detection system about the $\theta$ axis. Such an oscillation need only cover an angle of, for example at the most 4 degrees. For a change-over between different measuring methods, the collimator system in a preferred embodiment is constructed so as to be exchangeable with a detection slit in the apparatus. The apparatus can thus be simply adapted to position-sensitive phase measurements, position-sensitive texture measurements, position-sensitive stress measurements, etc. Notably the width of the detection slit is adapted to a desired resolution. Similarly, the resolution of the position-sensitive detector per se may be adapted to a desired resolution of the apparatus in the dispersion direction.

Some preferred embodiments in accordance with the invention will be described in detail hereinafter with reference to the drawing. Therein:

Figure 1:
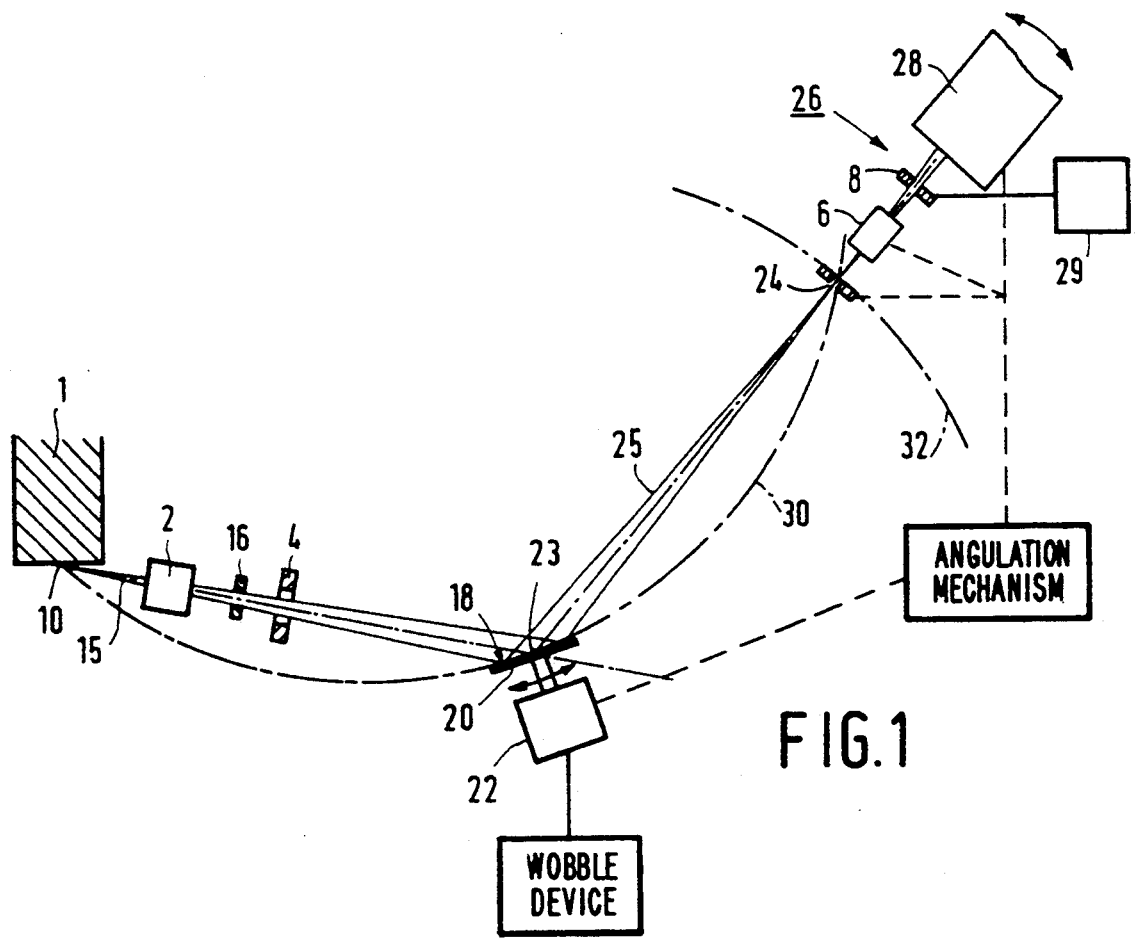
FIG. 1 shows diagrammatically the construction of an apparatus in accordance with the invention, drawn in the diffraction plane.

The Figures show an X-ray analysis apparatus in accordance with the invention, comprising an X-ray source of which only an anode 1 is shown, said anode having a line focus 10 which is shown to extend transversely of the plane of drawing. An X-ray beam emanating from the line focus 10 impinges, after having passed an entrance slit 16 which is also referred to as a divergence slit, on a surface 18 of an object 20 mounted on a goniometer device 22. At the area of the object, the X-ray beam 15 has a rectangular cross-section so that a likewise rectangular sub-area 23 of the object is irradiated. A beam 25 diffracted from the object is incident, after passage through a detection slit 24, on a detection device 26 comprising a linear position-sensitive detector 28 for position-sensitive measurement of the intensity of X-rays emanating from the object. For the sake of clarity, the longitudinal direction, i.e. the position-sensitive direction of the detector, is oriented transversely of the plane of drawing of FIG. 1. A device 29 for detection signal recording, processing and/or display is associated with the detection device 26. The goniometer device 22 is, for example suitable for translation in x, y and z directions, but usually only for an x and an y translation. The goniometer may also be suitable for object rotation about the z axis, for object tilting about the x axis and/or the y axis, and for the previously mentioned object oscillation.

In the beam path between the line focus 10 and the object there may also be provided an entrance Soller slit system 2 and a radiation grid 4. The detection device 26 may comprise a detection Soller slit system 6 and a scattered radiation grid 8. FIG. 1 also shows a focus circle or Rowland circle 30. The line focus 10, the centre of the object and the detection slit are situated on the focus circle for all measurement points. A diffraction circle 32 represents a path of motion for the detection slit during the $2\theta$ angulation. The diffraction plane in this case coincides with the plane of drawing and extends transversely of the line focus 10 and through the centre of the beam 15, 25.

Figure 2:
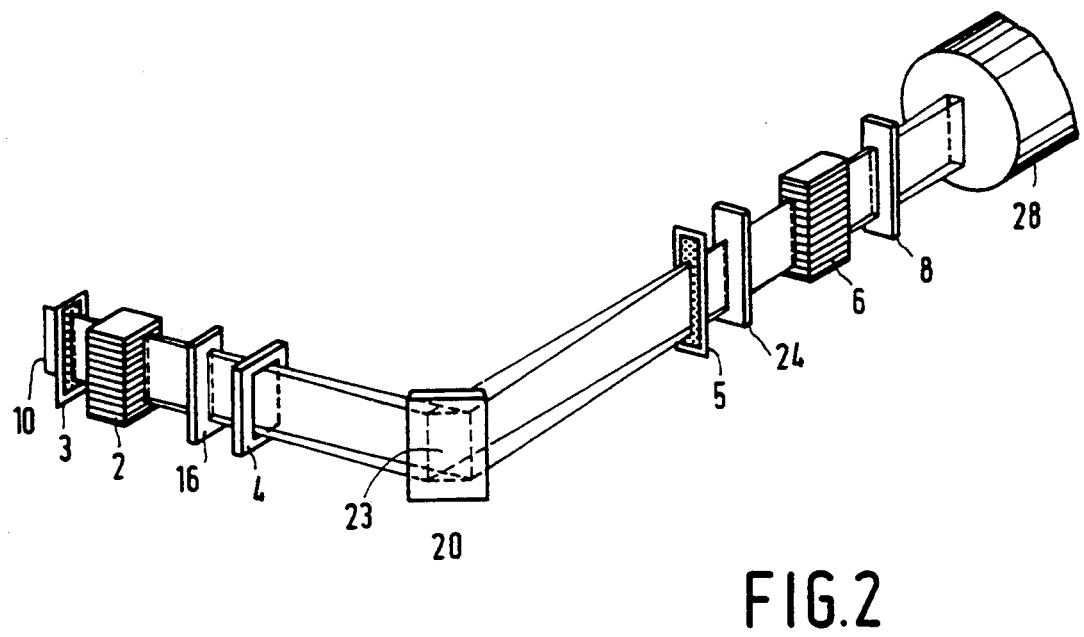
FIG. 2 is a more perspective view of the same apparatus.
Figure 3:
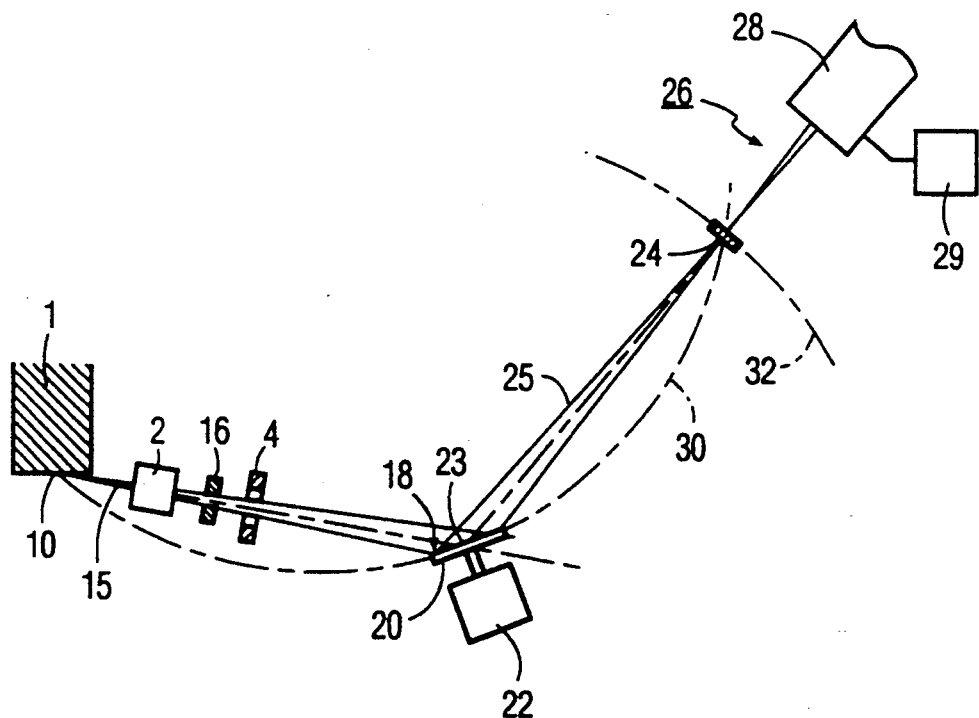
FIG. 3 shows an alternative embodiment of the invention.
Figure 4:
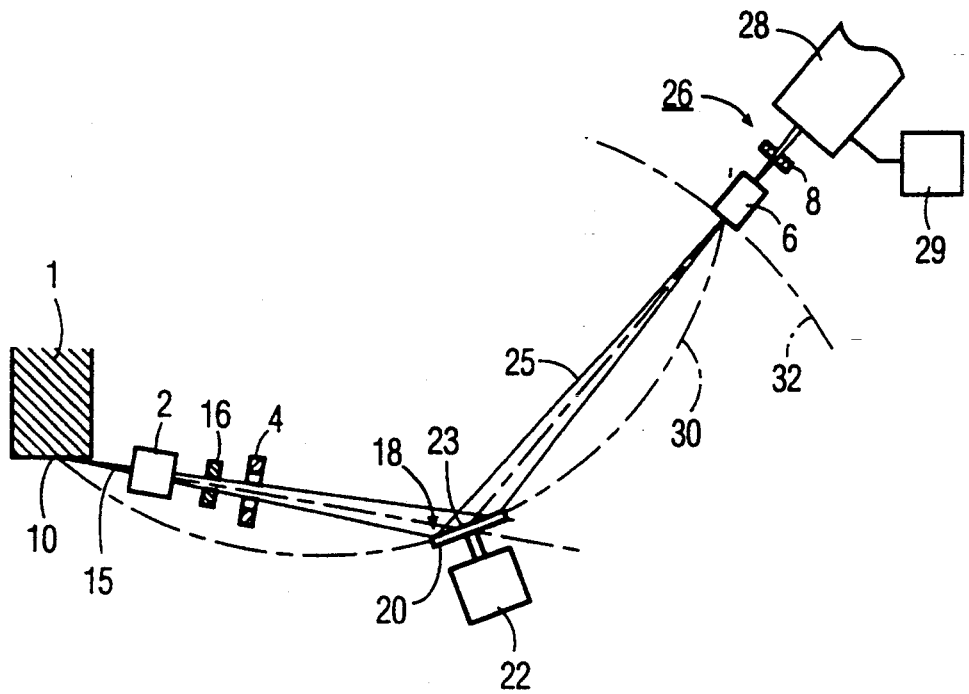
FIG. 4 shows a second alternative embodiment of the invention.

For example, an X-ray tube having a line focus of, generally speaking, for example $0.1 \times 10$ mm$^2$, and a linear position-sensitive detector arranged parallel to the $2\theta$ axis, enables position-sensitive measurement. For the direction transversely of the $2\theta$ axis, i.e. transversely of the longitudinal direction of the detector, position-sensitivity is achieved by means of the detection slit 24. A collimator system 6 has a dimension of, for example at the most 5 mm in the $2\theta$ direction and consists of plates having a thickness of, for example 50–100 $\mu$m and a pitch of, for example 0.1 to 10 mm. Because of the limited dimension of the collimator system to be used, it can be constructed so as to be comparatively simply exchangeable or adjustable, enabling adjustment of the resolution in the relevant direction. The resolution in the other direction is determined completely by the dimension of the detection elements of the position-sensitive detector 28. The dimension thereof can be comparatively small in said direction in the case of a linear position-sensitive detector, for example approximately 50–150 $\mu$m. For the $2\theta$ angulation, the width of a detection slit to be used can then be optimally adjusted. FIG. 2 also shows an entrance radiation filter and a detection radiation filter 5 arranged in the beam path.

I claim:

1. X-ray analysis apparatus comprising:
   (a) an X-ray source for generating an X-ray beam,
   (b) means for supporting an object to be analyzed,
   (c) a detection system for X-rays, from said object, said detection system comprising a one-dimensional, position-sensitive detector,
   (d) a detection collimator system located in front of the one-dimensional position-sensitive detector;
   (e) said X-ray source, object, and detection collimator system lying on a focus circle of the apparatus,
   (f) an angulation mechanism connected to the object supporting means, the detection system, and the detection collimator system for rotating the object and the detection system and the detection collimator system to maintain the object and detection collimator system on the focus circle,
   (g) said X-ray beam irradiating a part of the object,
   (h) said one-dimensional position-sensitive detector and said detection collimator system being arranged and oriented with respect to one another and to the X-ray beam such that position-sensitive analysis of radiation incident on the detection collimator system is carried out for a number of positions in parallel.

2. X-ray analysis apparatus as claimed in claim 1, wherein the X-ray source, object and detection collimator system form a diffraction plane, the position-sensitive direction of the one-dimensional position-sensitive detector extending transversely to the diffraction plane.

3. X-ray analysis apparatus as claimed in claim 2, wherein the detection collimator system comprises a longitudinal detection slit oriented so as to extend in the position-sensitive direction of the one-dimensional position-sensitive detector.

4. X-ray analysis apparatus as claimed in claim 3, further comprising an additional collimator arranged after the detection collimator system and before the one-dimensional position-sensitive detector for position selection of the object part to be analyzed.

5. X-ray analysis apparatus as claimed in claim 2, further comprising a wobble device connected to the object supporting means for tilting the object up to approximately $\pm 2°$.

6. X-ray analysis apparatus as claimed in claim 4, wherein the additional collimator comprises a pile of plates forming slits extending parallel to the width of the longitudinal detection slit.

7. X-ray analysis apparatus as claimed in claim 6, wherein the X-ray source forms a line focus that extends parallel to the longitudinal direction of the detection slit.

8. X-ray analysis apparatus as claimed in claim 1, wherein the one-dimensional position-sensitive detector comprises elements having dimensions of 50–150 micrometers.

9. X-ray analysis apparatus as claimed in claim 2, wherein the detection collimator system comprises a Soller slit system oriented parallel to the diffraction plane, whereby the position-sensitive detector simultaneously analyzes various positions of the irradiated part of the object.

10. X-ray analysis apparatus comprising:
   a) an X-ray source for generating an X-ray beam;
   b) means for supporting an object to be analyzed, so that the x-ray beam irradiates a part of the object;
   c) detection system for X-rays, said detection system comprising a one-dimensional position sensitive detetor, said X-ray source, object and detection system forming a diffraction plane, the position sensitive direction of the one-dimensional position sensitive detector extending transversely to the diffraction plane;
   d) a longitudinal detection slit oriented so as to extend in the position-sensitive direction of the one-dimensional position-sensitive detector, whereby the one-dimensional position-sensitive detector measures variations in diffraction lines in the longitudinal direction of the slit; and
   e) an angulation mechanism connected to the object supporting means, the detection system, and the slit, for rotating the object, the detection system, and the slit to maintain the object and the slit on a focus circle of the apparatus.

* * * * *